United States Patent [19]

Cole et al.

[11] 4,160,861

[45] Jul. 10, 1979

[54] METHOD FOR THE SEPARATION OF ANTIBIOTIC MACROLIDES

[75] Inventors: Douglas L. Cole, Roselle Park; Robert T. Goegelman, Linden, both of N.J.

[73] Assignee: Merck & Co., Inc., Rahway, N.J.

[21] Appl. No.: 839,138

[22] Filed: Oct. 3, 1977

[51] Int. Cl.$^2$ ............................................ C07H 17/08
[52] U.S. Cl. ............................... 536/17 A; 195/80 R; 424/181; 435/76; 435/886
[58] Field of Search ...................... 260/343.41; 536/17

[56] References Cited
U.S. PATENT DOCUMENTS 3,950,360  4/1976  Aoki et al. .................... 260/343.41

OTHER PUBLICATIONS

Mishima et al. Tetrahedron letters, No. 10, pp. 711–714, 1975.
Journal of Antibiotics 29 (6), Jun. 1976, pp. 76–35 to 76–42 and pp. 76–14 to 16.

*Primary Examiner*—Natalie Trousof
*Assistant Examiner*—Jane T. Fan
*Attorney, Agent, or Firm*—David L. Rose; Richard A. Thompson; Harry E. Westlake

[57] ABSTRACT

This case relates to a novel process which aids in the isolation and purification of novel compounds which are produced by the microorganism, *Streptomyces avermitilis*. The process described herein utilizes a high pressure liquid chromatographic system (HPLC) for the isolation and purification of the active compound. The compounds which are isolated and purified are described generically as C-076 and have significant parasiticidal activity.

8 Claims, No Drawings

METHOD FOR THE SEPARATION OF ANTIBIOTIC MACROLIDES

SUMMARY OF THE INVENTION

This invention is directed to a process for isolating the novel chemical compounds C-076 which are produced by the fermentation of a nutrient medium with a strain of the microorganism, *Streptomyces avermitilis*.

The compounds, to which the novel techniques of isolation and purification of this invention are directed, are described in co-pending U.S. application Ser. No. 772,601 of G. Albers-Schonberg, R. Burg, T. Miller, R. Ormond and H. Wallich. Said application teaches the use and characterization of the C-076 compounds as well as the utilization and characterization of the microorganism, *Streptomyces avermitilis*. Said application is hereby incorporated by reference in this application.

More particularly, this invention is comprised of a novel technique wherein it is an object of this process to aid in the isolation of the parasiticidal active compound in a substantially purified form. Further objects of this invention will become apparent from the following description.

DESCRIPTION OF THE INVENTION

In accordance with this invention, techniques of extraction and fractionation are utilized to isolate and purify substances generically described herein as C-076. These substances are prepared by growing under controlled conditions strains of microorganisms of *Streptomyces avermitilis*. These substances are described as C-076 A1a, A1b, A2a, A2b, B1b, B2a, and B2b.

Based on taxonomic studies, the microorganisms capable of producing these C-076 compounds are of a new species of the genus Streptomyces, which has been named *Streptomyces avermitilis*. One such culture, isolated from soil is designated MA-4680 in the culture collection of MERCK & CO., Inc., Rahway, N.J. A C-076 producing sample of this culture has been deposited in the permanent culture collection of the Fermentation Section of the Northern Utilization Research Branch, U.S. Department of Agriculture at Peoria, Ill., and has been assigned the accession number NRRL 8165. A sample of NRRL 8165 has also been deposited, without restriction as to availability, in the permanent culture collection of the American Type Culture Collection at 12301 Parklawn Drive, Rockville, Md. 20852, and has been assigned the accession number ATCC 31,267.

However, the present invention also embraces mutants of the above described microorganism. For example, those C-076 producing mutants which are obtained by natural selection or those produced by mutating agents including X-ray irradiation, ultraviolet irradiation, nitrogen mustard or like treatments are also included within the ambit of this invention.

One example of such an organism is a strain of *Streptomyces avermitilis* MA 4848 which was isolated after irradiation with ultraviolet light of *Streptomyces avermitilis* MA 4680. A lyophilized tube and a frozen vial of this culture has been deposited in the permanent culture collection of the American Type Culture Collection, and they have been assigned the accession numbers 31271 respectively. Slightly higher fermentation yields of C-076 have been obtained using this frozen stock as inoculum.

In particular, this invention is directed to a method for the separation of C-076 components wherein a solution or broth containing said components is chromatographed on a reverse phase high pressure liquid chromatography column. Also in connection with the process is the use of an elution solvent which is 85:15 methanol:water (v/v).

The high pressure liquid chromatographic system used herein may be used to quantitatively assay C-076 B1, B2, A1 and A2 in extracts of fermentation broth and in mixtures produced during the purification process.

The C-076 compounds are produced during the aerobic fermentation of suitable aqueous nutrient media under conditions described hereinafter, with a producing strain of *Streptomyces avermitilis*. Aqueous media such as those used for the production of many antibiotic substances are suitable for use in this process for the preparation of C-076.

Such nutrient media contain sources of carbon and nitrogen assimilable by the microorganism and generally low levels of inorganic salts. In addition, the fermentation media may contain traces of metals necessary for the growth of the microorganisms. These are usually present in sufficient concentration in the complex sources of carbon and nitrogen which may be used as nutrient sources, but can, of course, be added separately to the medium if desired.

In general, carbohydrates such as sugars, for example dextrose, sucrose, maltose, lactose, dextran, cerelose and the like, and starches are suitable sources of assimilable carbon in the nutrient media. The exact quantity of the carbon source which is utilized in the medium will depend, in part, upon the other ingredients in the medium but it is usually found that an amount of carbohydrate between about 0.5 and 5% by weight of the medium is satisfactory. These carbon sources can be used individually or several such carbon sources may be combined in the same medium.

Various nitrogen sources such as yeast hydrolysates, yeast autolysate, soybean meal, casein hydrolysates, yeast extracts, corn steep liquors, distillers solubles, cottonseed meal, meat extract and the like, are readily assimilable by *Streptomyces avermitilis* in the production of the C-076 compounds. The various sources of nitrogen can be used alone or in combination in amounts ranging from about 0.2 to 6% by weight of the medium.

Among the nutrient inorganic salts which can be incorporated in the culture media are the customary salts capable of yielding sodium, potassium, magnesium, ammonium, calcium, phosphate, sulfate, chloride, carbonate and like ions. Also included are trace metals such as cobalt, manganese, iron and the like.

The fermentation employing the C-076-producing microorganisms can be conducted at temperatures ranging from about 20° C. to about 40° C. For optimum results, it is most convenient to conduct these fermentations at a temperature in the range of from about 24° C. to about 30° C. Temperatures of about 27° C.–28° C. are most preferred. The pH of the nutrient medium suitable for producing the C-076 compounds can vary from about 5.0 to 9.0 with a preferred range of from about 6.0 to 7.5.

Small scale fermentations are conveniently carried out by placing suitable quantities of nutrient medium in a flask employing known sterile techniques, inoculating the flask with either spores or vegetative cellular growth of a C-076-producing strain of *Streptomyces avermitilis*, loosely stoppering the necks of the flask with cotton, and permitting the fermentation to proceed in a constant room temperature of about 28° C. on a rotary shaker for about 3 to 10 days. For larger scale work, it is preferable to conduct the fermentation in suitable tanks provided with an agitator and a means of aerating the fermentation medium. The nutrient medium is made up in the tank and after sterilization is inoculated with a suitable source of vegetative cellular growth of a C-076 producing strain of *Streptomyces avermitilis*. The fermentation is allowed to continue for from 1 to 8 days while agitating and/or aerating the nutrient medium at a temperature in the range of from about 24° C. to 37° C. The degree of aeration is dependent upon several factors such as the size of the fermentor, agitation speed and the like. Generally, the larger scale fermentations are agitated at about 95 to 150 rpm and about 2 to 20 cubic feet per minute of air.

The substances to which the novel process of this invention are utilized, are generically referred to herein as C-076, and are found primarily in the mycelium on termination of the *Streptomyces avermitilis* fermentation, and may be recovered and separated from one another as described below. Four major and four minor components of the C-076 as elaborated by *Streptomyces avermitilis* have been isolated. The eight different compounds are identified herein as C-076 A1a, A1b, A2a, A2b, B1a, B1b, B2a and B2b.

Based on experimental data, the C-076 compounds are believed to have the following planar structural formula:

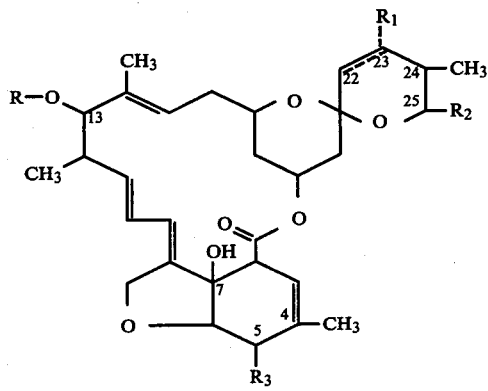

wherein R is the α-L-oleandrosyl-α-L-oleandroside of the structure:

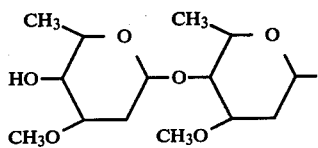

and wherein the broken line indicates a single or a double bond;

$R_1$ is hydroxy and is present only when said broken line indicates a single bond.

$R_2$ is propyl or butyl; and $R_3$ is methoxy or hydroxy.

In the foregoing structural formula, the individual compounds are as set forth in Table IV.

TABLE IV

|  | $R_1$ | $R_2$ | $R_3$ |
|---|---|---|---|
| A1a | Double bond | butyl | —OCH₃ |
| A1b | Double bond | propyl | —OCH₃ |
| A2a | —OH | butyl | —OCH₃ |
| A2b | —OH | propyl | —OCH₃ |
| B1a | Double bond | butyl | —OH |
| B1b | Double bond | propyl | —OH |
| B2a | —OH | butyl | —OH |
| B2b | —OH | propyl | —OH |

The major C-076 compounds are not produced in equal amounts by the fermentations described herein. In general, it has been found that the A1 compounds comprise about 20 to 30% by weight of the total C-076 complex produced, the A2 compounds about 1 to 20% and the B1 and B2 compounds each about 25 to 35%.

The separation of the C-076 series of compounds from the whole fermentation broth and the recovery of the individual components is carried out by solvent extraction and application of chromatographic fractionations with various chromatographic techniques and solvent systems.

The C-076 compounds have slight solubility in water, but are soluble in organic solvents. This property may be conveniently employed to recover them from the fermentation broth. Thus in one recovery method, the whole fermentation broth is filtered and the aqueous filtrate discarded. The wet mycelial cake is then extracted with an appropriate organic solvent. While any organic solvent may be employed, it is preferable to use a water miscible solvent such as acetone, methanol, ethanol and the like. Generally, several extractions are desirable to achieve maximum recovery. The solvent removes the C-076 active components as well as other substances lacking the antiparasitic activity of C-076. If the solvent is a water miscible one, the water is also removed from the wet mycelia. The extracted mycelia may be discarded. The solvent extracts are evaporated to remove the organic solvent and extracted several times with a second solvent. When the first extraction employs a water miscible solvent, the second extraction preferably employs a water immiscible solvent such as chloroform, methylene chloride, carbon tetrachloride, ethylacetate, methylethyl ketone, methylisobutyl ketone and the like. These latter extracts are dried and concentrated using known techniques to afford a residue comprising C-076 admixed with other materials. This fraction is then conveniently chromatographed in order to separate the active C-076 compounds from other material and also to separate and isolate the individual C-076 compounds. The chromatographic techniques which may be employed to purify the C-076 compounds are generally known to those skilled in this art.

It is the utilization of high pressure liquid chromatography with the equipment, elution solvent and temperature that provide a unique and quantitative method for rapidly separating the major C-076 components.

The elution solvent utilized in the instant invention may be a mixture of methanol:water (v/v) ranging in composition of from 80:20 to about 90:10, respectively. The preferred methanol:water (v/v) is 85:15.

The column temperature may range from 25° C. to 40° C. The preferred temperature is 40° C.

The following examples are capable of wide variation and modification and any minor departure or extension is considered as being within the skill of the artisan and as falling within the scope of this invention.

EXAMPLE 1

A 250-ml. baffled Erlenmeyer flask containing 50 ml. of the following medium:

| Lactose | 2.0% |
|---|---|
| Distiller's Solubles | 1.5% |
| Autolyzed yeast, Ardamine pH | 0.5% |
| pH-before sterilization | 7.0 | is inoculated with the contents of one frozen vial of *Streptomyces avermitilis* MA-4848 and incubated on a rotary shaker at 28° C. for 24 hours at 150 rpm.

Ten ml. of the above fermentation media is employed to inoculate 500 ml. of the same medium as above in a 2-liter baffled Erlenmeyer flask. The fermentation media is incubated at 150° rpm on a rotary shaker at 28° C. for 24 hours.

All of the foregoing media is employed to inoculate 467 liters of the following media in a 756-liter stainless steel fermentor:

| Lactose | 2.0% |
|---|---|
| Distiller's Solubles | 1.5% |
| Autolyzed yeast, Ardamine pH | 0.5% |
| Polyglycol 2000 | 0.32 ml./liter |
| pH-before sterilization | 7.0 |

The fermentation media is incubated at 28° C. for 40 hours with an air flow of 10 cubic feet per minute and an agitation rate of 130 rpm.

230 Liters of the above media is employed to inoculate 4,310 liters of the following medium in a 5,670-liter stainless steel fermentor:

| Dextrose | 4.5% | |
|---|---|---|
| Peptonized Milk | 2.4% | |
| Autolyzed yeast, Ardamine pH | 0.25% | |
| Polyglycol 2000 | 2.5 | ml./liter |
| pH--before sterilization | 7.0 | |

The fermentation continues for 144 hours at 26° C. with an air flow rate of 54.3 cubic feet per minute and agitation rate of 120 rpm.

The fermentation media are filtered and the mycelial filter cake washed with about 550 liters of water, the filtrate and washings are discarded. The filter cake is agitated with about 1500 liters of acetone for about one hour and filtered. The filter cake is washed with a mixture of about 150 liters of acetone and 40 liters of deionized water affording about 2000 liters of extract.

The foregoing fermentation and extraction is repeated on the same scale affording a further 200 liters of acetone extract which is combined with the first extract and evaporated to a volume of about 800 liters. The pH of the concentrate is adjusted to about 4.7 with concentrated hydrochloric acid and combined with about 800 liters of methylene chloride. The combined solvents are agitated for about 4 hours and separated. The aqueous layer is combined with an additional 800 liters of methylene chloride and agitated for about 4 hours. The layers are separated and each methylene chloride extract separately treated with about 10 kilograms of Super-Cel and filtered. Both extracts are evaporated to a combined volume of about 60 liters.

EXAMPLE 2

A mixture of all 8 C-076 components are chromatographed on a high pressure liquid chromatography column 4 mm.×30 cm. packed with 10 micron $\mu$ Bondapak $C_{18}$ silica gel (available from Waters Associates Inc., Maple St., Milford, Mass. 01757) eluting with 85:15 (v/v) methanol:water at a constant column temperature of 40° C. At a flow rate of 1.2 ml. per minute all 8 compounds are separated and the elution volumes, which under the foregoing constant conditions are characteristic of the individual compounds are as follows:

| | Elution Volume (Ve) Ml. |
|---|---|
| C-076 B2b | 5.90 |
| C-076 B2a | 6.52 |
| C-076 A2b | 7.12 |
| C-076 A2a | 7.88 |
| C-076 B1b | 8.36 |
| C-076 B1a | 9.60 |
| C-076 A1b | 10.24 |
| C-076 A1a | 11.88 |

The separation of C-076 "b" components from the respective "a" components is accomplished using techniques such as high pressure liquid chromatography. An absolute methanol solution of 30 microliters of a mixture of C-076 A1a and A1b, estimated to contain 30 micrograms of C-076 A1b is placed on a 3×250 mm. high pressure liquid chromatography column containing Spherisorb 5 micron ODS (available from Spectra Physics) as packing. The column is eluted with 85:15 methanol:water at a rate of 0.15 ml./min. The elution of the products are followed by observing the ultraviolet absorption of the eluent and collecting the individual components at the outlet of the UV monitor. Thirty micrograms of C-076 A1b is recovered and analyzed in a mass spectrometer.

This process is also employed wherein the same and larger particle diameter $C_{18}$ silica gel or other similar reverse phase gels (up to 125 micron diameter) can be utilized in columns of diameter up to one inch. Also, the column may be up to eight feet in length with sample loadings up to 5 g. per chromatographic run. Further increases in the scale of these preparative chromatographic columns are also possible.

At high sample loadings, water may be replaced in the eluent solutions by ethylene glycol at similar concentrations, thereby enhancing solubility of C-076 without markedly changing the elution characteristics of the column. Maximal sample capacity of a given column is increased in this way by a factor of approximately three.

It can also be appreciated by those skilled in the art that other solvents can be utilized with water as the elution solvent. Other solvents that can be utilized with the water are ethanol, propanol, tetrahydrofuran, acetonitrile and the like.

What is claimed is:

1. A method for the separation of C-076 components wherein said C-076 components have the formula:

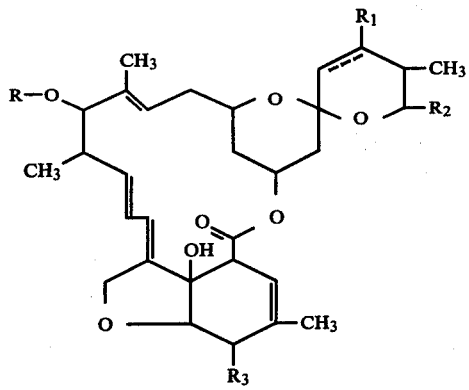

wherein
R is:

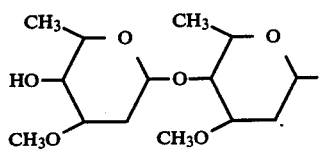

and wherein the broken line indicates a single or a double bond;
$R_1$ is hydroxy and is present only when said broken line indicates a single bond.
$R_2$ is propyl or butyl; and
$R_3$ is methoxy or hydroxy, from a solution or broth containing a mixture of C-076 components obtained from the fermentation of a C-076 producing strain of Streptomyces avermitilis, wherein said solution or broth is chromatographed on a reverse hase high pressure liquid chromoatography column and wherein the elution solvent is methanol:-water.

2. A process according to claim 1 wherein the methanol:water is from 80:20 to 90:10.

3. A process according to claim 1 wherein the methanol:water ratio is 85:15.

4. A process according to claim 1 wherein the column temperature is from 25° C. to about 40° C.

5. A process according to claim 1 wherein the column temperature is 40° C.

6. A process according to claim 1 wherein the methanol:water ratio is 85:15 and the column temperature is 40° C.

7. A process according to claim 1 wherein the column packing is silica gel.

8. A method for the separation of C-076 components wherein said C-076 components have the formula:

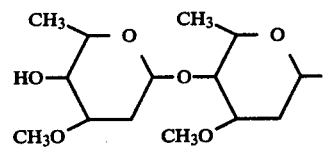

wherein
R is:

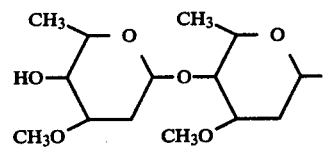

and wherein the broken line indicates a single or a double bond;
$R_1$ is hydroxy and is present only when said broken line indicates a single bond.
$R_2$ is propyl or butyl; and
$R_3$ is methoxy or hydroxy, from a solution or broth containing a mixture of C-076 components, wherein said solution or broth is chromatographed on a reverse phase high-pressure liquid chromatography column and wherein the elution solvent is methanol: ethyleneglycol.

* * * * *